(12) United States Patent
Schreiber et al.

(10) Patent No.: US 9,411,141 B2
(45) Date of Patent: Aug. 9, 2016

(54) MICROSCOPE AND A METHOD FOR EXAMINING A SAMPLE USING A MICROSCOPE

(71) Applicant: LEICA MICROSYSTEMS CMS GMBH, Wetzlar (DE)

(72) Inventors: Frank Schreiber, Dossenheim (DE); Lioba Kuschel, Mannheim (DE); Patric Mrawek, Neustadt (DE); Bernd Widzgowski, Dossenheim (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 14/436,919

(22) PCT Filed: Sep. 27, 2013

(86) PCT No.: PCT/DE2013/200195
§ 371 (c)(1),
(2) Date: Apr. 20, 2015

(87) PCT Pub. No.: WO2014/059983
PCT Pub. Date: Apr. 24, 2014

(65) Prior Publication Data
US 2015/0286040 A1    Oct. 8, 2015

(30) Foreign Application Priority Data
Oct. 19, 2012    (DE) .......................... 10 2012 219 136

(51) Int. Cl.
*G01J 1/58*        (2006.01)
*G01T 1/10*        (2006.01)
*G02B 21/00*       (2006.01)
(Continued)

(52) U.S. Cl.
CPC ........ *G02B 21/0064* (2013.01); *G01N 21/6486* (2013.01); *G02B 21/008* (2013.01); *G02B 21/0076* (2013.01); *G02B 21/0084* (2013.01);
(Continued)

(58) Field of Classification Search
CPC ............................... G02B 21/00; G01N 21/64
USPC .......................................... 250/459.1, 458.1
See application file for complete search history.

(56) References Cited

U.S. PATENT DOCUMENTS 7,009,699 B2    3/2006   Wolleschensky et al.
7,688,442 B2    3/2010   Wolleschensky et al.
(Continued)

FOREIGN PATENT DOCUMENTS

DE           10151217 A1    4/2003
DE       102004017956 A1   11/2005
(Continued)

*Primary Examiner* — David Porta
*Assistant Examiner* — Meenakshi Sahu
(74) *Attorney, Agent, or Firm* — Leydig, Voit & Mayer, Ltd.

(57) ABSTRACT

A microscope, in particular a confocal microscope, has one or more lasers for generating an illumination light for a sample and has a detection device for detected signals from the sample. The detection device includes multiple adjustable spectral detection channels for the detection of predefinable different wavelength regions, and is configured and refined in the interest of particularly versatile utilization in consideration of a wide variety of phenomena, with particularly good separation of the phenomena in the context of investigation, in such a way that multiple temporal detection windows are respectively settable for the spectral detection channels.

19 Claims, 12 Drawing Sheets

(51) Int. Cl.
  *G02B 21/16* (2006.01)
  *G02B 21/36* (2006.01)
  *G01N 21/64* (2006.01)

(52) U.S. Cl.
  CPC .............. *G02B 21/16* (2013.01); *G02B 21/365* (2013.01); *G01N 2201/0612* (2013.01)

(56) References Cited

U.S. PATENT DOCUMENTS

| | | |
|---|---|---|
| 2002/0052048 A1 | 5/2002 | Stein et al. |
| 2003/0151741 A1 | 8/2003 | Wolleschensky et al. |
| 2005/0230610 A1 | 10/2005 | Schreiber |
| 2010/0294949 A1* | 11/2010 | Sasaki ................ G02B 21/0076 250/458.1 |
| 2011/0042580 A1* | 2/2011 | Wilson ................ G01N 21/6456 250/458.1 |

FOREIGN PATENT DOCUMENTS

| | | |
|---|---|---|
| EP | 1202050 A2 | 5/2002 |
| EP | 1308715 A1 | 5/2003 |
| EP | 1669789 A1 | 6/2006 |
| EP | 2253983 A2 | 11/2010 |
| WO | WO 2004113987 A1 | 12/2004 |

* cited by examiner

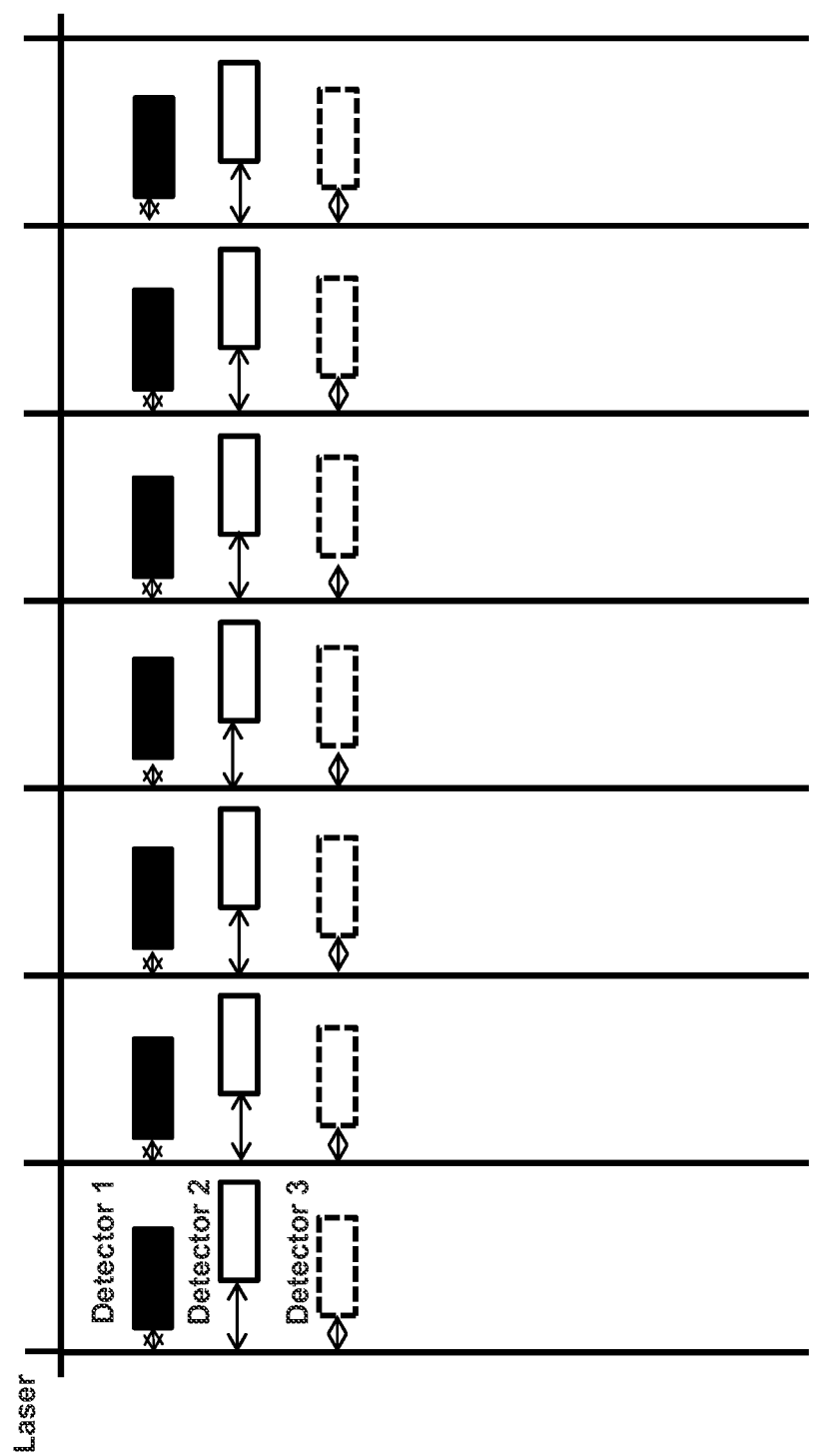

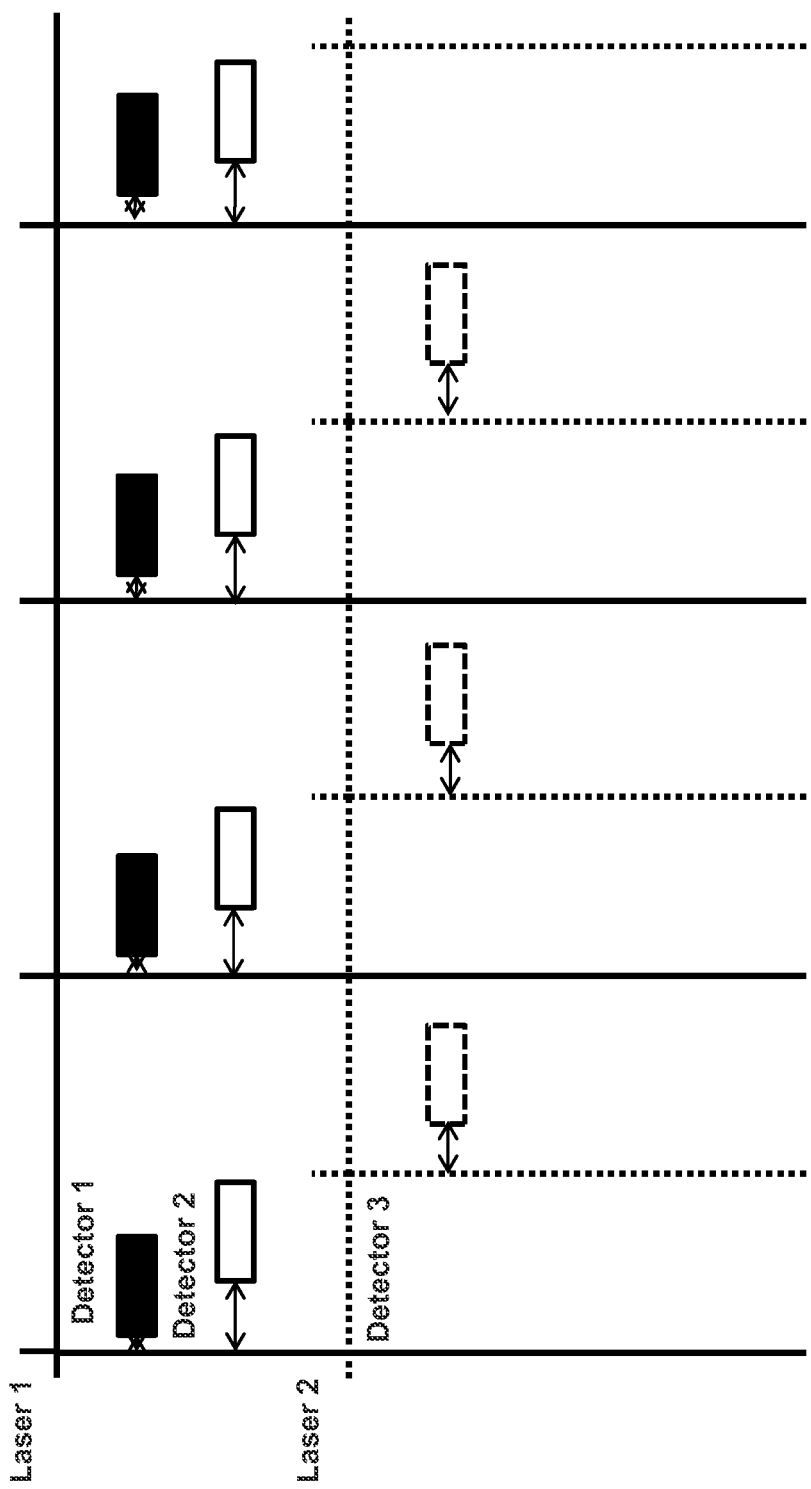

MICROSCOPE AND A METHOD FOR EXAMINING A SAMPLE USING A MICROSCOPE

CROSS-REFERENCE TO RELATED APPLICATIONS

This application is a U.S. National Stage Application under 35 U.S.C. §371 of International Application No. PCT/DE2013/200195 filed on Sep. 27, 2013, and claims benefit to German Patent Application Nos. DE 10 2012 219 136.4 filed on Oct. 19, 2012. The International Application was published in German on Apr. 24, 2014, as WO 2014/059983 A1 under PCT Article 21(2).

FIELD

The present invention relates to a microscope, in particular a confocal microscope, having one or more lasers for generating an illumination light for a sample.

BACKGROUND

Microscopes of the kind recited above, and methods for investigating a sample using such a microscope, are known from practical use and exist in a wide variety of embodiments. In confocal laser microscopy, for example, biological samples are usually labeled with dyes. Different organelles are often labeled with different dyes. These dyes are excited, with an illumination light generated by means of a laser or multiple lasers, to emit light. If multiple dyes are present in the sample, they must usually be depicted on different image channels by means of a wavelength separation in the detection device. The corresponding detected signals pass through detection channels that are settable or embodied for the detection of predefinable different wavelength regions.

The emission spectra of the dyes often overlap. In addition, the reflected excitation light usually falls within the emission spectra of the dyes. Phenomena such as autofluorescence, second harmonic generation, or resonant energy transfer also cannot be distinguished from "normal" fluorescence photons only by wavelength separation. Because these phenomena either furnish additional information about the sample or create an interfering overlay on the pure fluorescence image, it is desirable to be able to separate these phenomena from the actual fluorescence signal in the context of detection.

With (for example, confocal) laser microscopes, the fluorescent light is often chromatically divided prior to detection. This is implemented either via a cascade of optical beam splitters, via a prism, or via an arrangement having a grating. After spectral division the light strikes different detectors in order to form different detection channels. A specific wavelength region is thus associated with each detector or detection channel.

In addition, two methods are known for measurements of fluorescence lifetimes. The first method is single-photon counting, the time between excitation and a detected signal being measured for each photon. Statistics are prepared here over a very large number of individual measurements. The goal here is to ascertain the decay curve and thus the lifetime of dye molecules. Because of the large quantities of data required, evaluation usually occurs offline. A rough estimate of the lifetimes is nevertheless also possible online, by averaging the measured individual values.

A second known method for measuring fluorescence lifetimes is represented by so-called gating methods, in which the photons are sorted into time windows specified before measurement. As with single-photon measurement, statistics are prepared so that the lifetime of the dyes can be calculated after measurement. The known gating methods carry out one measurement for each gating window.

SUMMARY

An aspect of the invention provides a microscope, comprising: a laser configured to generate an illumination light for a sample; and a detection device configured to detect a signal from the sample, wherein the detection device includes two or more adjustable spectral detection channels configured to detect predefinable different wavelength regions, and wherein two or more temporal detection windows are respectively settable for the spectral detection channels.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 8a schematically depicts the relationship of detection windows of different detectors to one laser;

FIG. 8b schematically depicts the relationship of detection windows of different detectors to various lasers;

DETAILED DESCRIPTION

Figure 1:
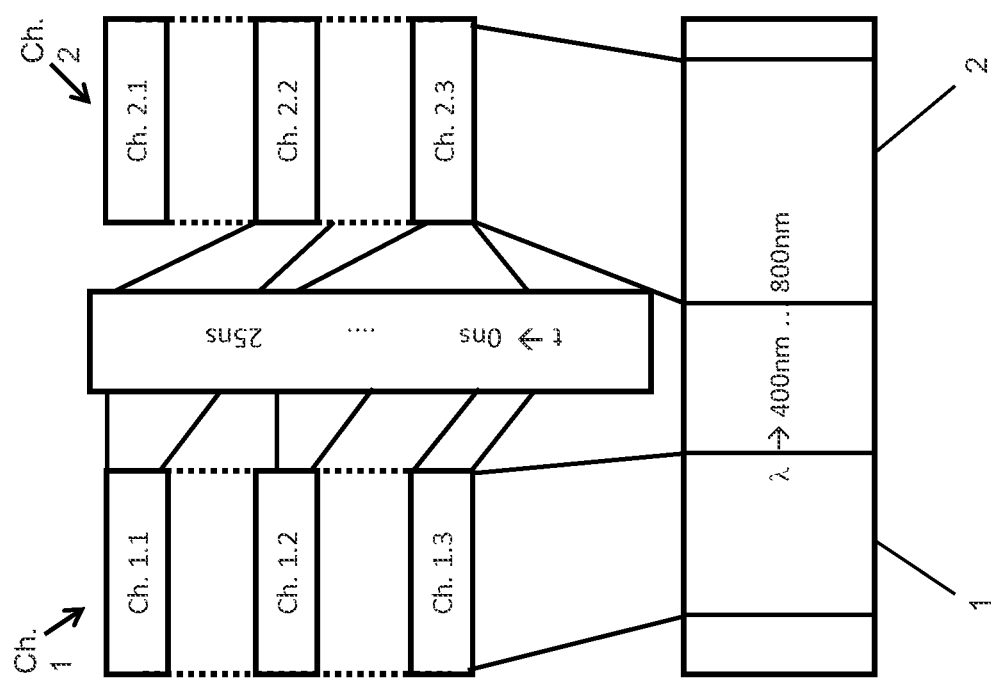
FIG. 1 schematically depicts a configuration according to the present invention of detection channels and associated temporal detection windows.

An aspect of the invention provides a microscope, in particular a confocal microscope, having one or more lasers for generating an illumination light for a sample and having a detection device for detected signals from the sample, the detection device comprising multiple adjustable spectral detection channels for the detection of predefinable different wavelength regions. A further aspect relates to a method for investigating a sample with a microscope, in particular a confocal microscope, the microscope comprising one or more lasers for generating an illumination light for a sample and comprising a detection device for detected signals from the sample, and the detection device comprising multiple adjustable spectral detection channels for the detection of predefinable different wavelength regions.

With the known microscopes and methods for investigating a sample it is problematic that many phenomena that transport information regarding the sample cannot be recognized in the context of detection. Detected signals of these phenomena are often suppressed without being used, or at least are reduced so they can no longer cause interference when measuring other phenomena. What occurs here is ultimately a waste of possible usable detected signals.

An aspect of the invention is based is therefore that of describing a microscope, and a method for investigating a sample with a microscope, of the kind recited previously, that enable particularly versatile utilization in consideration of a wide variety of phenomena, with particularly good separation of the phenomena in the context of investigation.

An aspect of the invention provides a microscope characterized by multiple temporal detection windows that are respective settable for the spectral detection channels; and the method is characterized by multiple temporal detection windows that are respectively settable for the spectral detection channels, and detected signals are thus acquired in the temporal detection windows.

What has been recognized in an aspect of the invention is firstly that thanks to a skillful design and execution of a measurement method, it is possible to distinguish from one another, and evaluate, a wide variety of phenomena during a sample investigation. For this purpose, concretely, multiple temporal detection windows are respectively settable for the spectral detection channels, and detection signals can then be acquired in the settable temporal detection windows. The time dependence of the detected signals is consequently taken into account, for example reflected light that occurs very quickly and fluorescent light that usually occurs only later. Thanks to a time separation performed in this regard by means of the temporal detection windows, mutual interference between the reflected signals and the fluorescence signals is very largely avoided. The two phenomena can thus be investigated and evaluated mutually independently. The microscope according to an aspect of the invention and the method according to an aspect of the invention thus make possible a dynamic interaction between wavelength selection and selection of the detected time window and thus, for example, enable optimization of the image contrast. It is furthermore possible, by combining both selection methods (wavelength and temporal detection window), to generate additional information, for example, in confocal image production. In particular, the user can immediately acquire visual feedback via the produced image, and optionally can optimize the settings of the detection channels and of the detection windows during the measurement itself.

The microscope according to an aspect of the invention and the method according to the present invention for investigating a sample consequently make possible particularly versatile utilization in consideration of a wide variety of phenomena, with particularly good separation of the phenomena during an investigation.

Concretely, the wavelength regions of the spectral detection channels could be adjustable and/or depictable during a measurement. Optimization of the measurement settings to the particular utilization instance is thereby enabled. Visual feedback via a produced image could be helpful here. Alternatively or in addition thereto, the temporal detection windows could be settable and/or depictable during a measurement. This too makes possible an adaptation to existing measurement situations in order to optimize, for example, image contrast. Graphic depiction simplifies measurement and makes it more convenient.

In a further advantageous embodiment, the wavelength regions could have a different size. This too enables optimization of the measurement conditions in terms of the particular utilization instance. Depending on the utilization instance, the wavelength regions could also be identical in size. Alternatively or in addition thereto, the temporal detection windows could each have a different size. This enables adaptation to individual time courses of detected signals.

In the interest of particularly convenient and versatile evaluation of the detected signals, a separate electronic evaluation system or a separate evaluation channel could be associated with each spectral detection channel. Alternatively thereto, multiple separate evaluation channels could be associated with each spectral detection channel so that evaluation can be adapted particularly flexibly to individual experimental situations. For additional flexibility, one temporal detection window or multiple temporal detection windows could be associated with each evaluation channel.

An evaluation of the detected signals to be acquired could occur in parallel or serially, depending on the utilization instance. Parallel evaluation is possible in the case of multiple separate evaluation channels associated with one spectral detection channel; a definable number of detection windows could furthermore be associated with each evaluation channel. A serial evaluation of the detected signals to be acquired could occur in the case of a single evaluation channel, in which case one detection window after another would need to be evaluated.

With additional advantage, the evaluation in the electronic evaluation system, in the evaluation channel, or in the evaluation channels could be activated or deactivated by means of control signals temporally correlating with the temporal detection windows. In the case in which evaluation is activated by the control signals, an evaluation takes place starting when the control signal is received. In the case of deactivation, an evaluation no longer takes place starting when the control signal is received. The suitable control process can be selected depending on the utilization instance, sometimes in the activation mode and sometimes in the deactivation mode.

With additional advantage, two or more temporal detection windows could be mutually correlatable during or after a data acquisition. The results of this correlation could preferably be depictable, for example by output on a display.

With additional advantage, different lasers could be associatable with different temporal detection windows. For example, in this context different lasers could be associatable with each temporal detection window or also with groups of temporal detection windows. Multiple lasers could also be respectively associatable with a single temporal detection window or with a group of temporal detection windows. The particular utilization instance is to be taken into account in this context.

Correspondingly, in a suitably embodied method for investigating a sample with the microscope, advantageously two or more temporal detection windows are correlated with one another during or after data acquisition, and then preferably the results of the correlation are depicted. In the same fashion, in a suitable method different lasers could be associated with different temporal detection windows.

In the case of a serial evaluation, an address counter could be incremented upon each deactivation of the control signal at the end of a temporal detection window. This makes possible separate depiction of the individual time segments during image acquisition. The evaluated image information for each time segment or each temporal detection window could be located in a separate memory cell as a result of the incrementing of the address counter. If multiple time segments or detection windows then need to be grouped together in a context of serial evaluation, as is already easily possible with parallel evaluation, this could readily be achieved, for serial evaluation as well, by subsequent correlation of the contents of the pertinent memory cells.

With serial evaluation of this kind as well, an inversion of the evaluation could be implemented, permitting controlled suppression of specific time segments of the image signal. For this, each memory cell containing an evaluated image information item of a temporal detection window could be equipped with an individually predefinable mark. This mark makes it possible, in the subsequent evaluation, to subtract the content of that time segment or detection window from the overall image.

In an additionally advantageous manner of evaluation, an evaluation of the detected signals to be acquired could be accomplished by means of a "track-and-hold" circuit, such that a data accumulation could be started with each start of a gating pulse.

In order for informative data to be obtained with the methods presented, it is useful on the one hand to acquire data at a high repetition rate and on the other hand to achieve high time resolution. Repetition rates of 80 MHz are favorable here. Both aforesaid requirements can be met in particularly advantageous fashion with a design implementation in a field programmable gate array (FPGA) or application specific integrated circuit (ASIC), the combination of an FPGA/ASIC, and as few extremely fast individual modules as possible for sampling or data acquisition, being particularly favorable.

In summary, it can be stated that image production in confocal laser microscopy has hitherto not taken into account a time dependence of the detected signals. Many phenomena that transport information regarding a sample therefore cannot be recognized in the detection process. In addition, the exclusive purpose of existing methods for measuring time-related phenomena in fluorescence microscopy is to quantitatively determine the lifetime of the dye molecules as exactly as possible. Adaptation of parameters during measurement is furthermore not provided for. In particular, a dynamic interaction between wavelength selection and selection of the detected time window is not possible with the known methods.

In an exemplifying embodiment of the present invention, the time or time window from excitation of a dye until arrival of the generated photons at the detector is used as an additional property of the detected photons. Because, for example, reflection, autofluorescence, and fluorescence differ in terms of this property, it thereby becomes possible to distinguish them from one another upon detection.

In the present exemplifying embodiment the temporal detection window is introduced in the context of image production in confocal laser microscopy, alongside the detection wavelength region, as a second criterion for the separation of detected signals. FIG. 1 schematically depicts for this purpose a possibility for setting up two separation channels Ch.1 and Ch.2 in a user interface. In the interest of clarity, both the number of wavelength regions 1 and 2 and the number of temporal detection windows Ch.1.1, Ch.1.2, and Ch.1.3, and Ch.2.1, Ch.2.2, and Ch.2.3 are limited in FIG. 1 respectively to two wavelength regions and three temporal detection windows per wavelength region or detection channel. Appreciably more wavelength regions and temporal detection windows can, however, be established.

Figure 2:
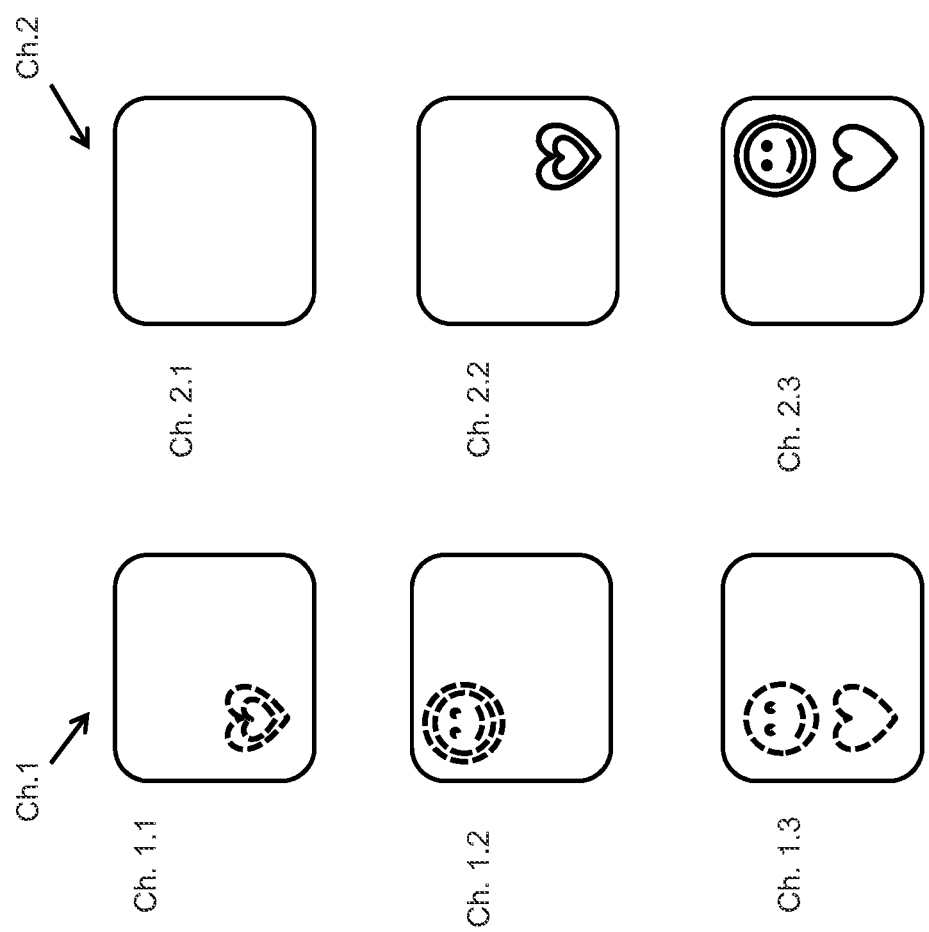
FIG. 2 is a schematic depiction with different detection windows and different detection channels, showing image data acquired with a configuration according to FIG. 1.

According to FIG. 2, an image produced in the context of the exemplifying embodiment described in FIG. 1 could be depicted as follows: Ch.1 receives only green light (dashed borders) and Ch.2 detects only red light (solid-line borders). In this example the single borders of the symbols in the detection windows represent the reflected light arriving very promptly, as depicted in Ch.1.3 and Ch.2.3. The symbols with double borders represent the fluorescence signal. What is depicted here by way of example is that the heart is a long-lived fluorescence, whereas the face is a short-lived fluorescence.

The following practical applications are possible, for example, in fluorescence microscopy (this is not an exhaustive listing):

A separation of fluorescent light and reflected light could be accomplished. A simultaneous depiction of the detection channels with superimposed wavelength regions in two or more detection channels can be implemented. On the one hand, reflected light can have an interfering effect on the image produced using the fluorescent light. On the other hand, the reflected image alone can furnish additional information, for example, regarding the position and location of optical interfaces. Simply suppressing the reflected signal would cause this information to be lost.

A further application area could be represented by the separation of second harmonic generation (SHG) and MP fluorescence. Just like reflection, the SHG signal is an extremely fast signal and can therefore easily be separated temporally from fluorescence. In contrast thereto, purely spectral separation can be difficult or impossible, especially when the emission wavelength of the fluorescence overlaps with the SHG wavelength. In particular with samples that bleach easily or with samples that move rapidly, it is advantageous if the user can simultaneously detect SHG and fluorescence signals and does not need to resort to two measurement operations.

A further application instance is constituted by the separation of autofluorescence and fluorescence. Autofluorescence often occurs with plant specimens. The lifetime and the wavelength of the autofluorescence are often very different. The temporal detection window, constituting an additional criterion, can simplify the separation of fluorescence and autofluorescence.

It is conceivable in principle that two or more temporal detection windows or detection channels can be mutually correlated during (online) or after (offline) data acquisition, and preferably the results of the correlation can be depicted. One example could be FRET depiction. With FRET, there is often only a slight decay in donor fluorescence with a simultaneous shortening of lifetime, while the acceptor exhibits a slight rise in intensity simultaneously with a flatter rising edge. If the intensity of the long-lived fluorescence of the donor is then divided by the short-lived intensity of the acceptor, this represents a more sensitive measurement method than one using only intensity measurements or only lifetime measurements. Other applications in which temporal detection windows or detection channels can be subtracted, added, multiplied, and/or mutually correlated in any way, are conceivable.

Figure 8C:
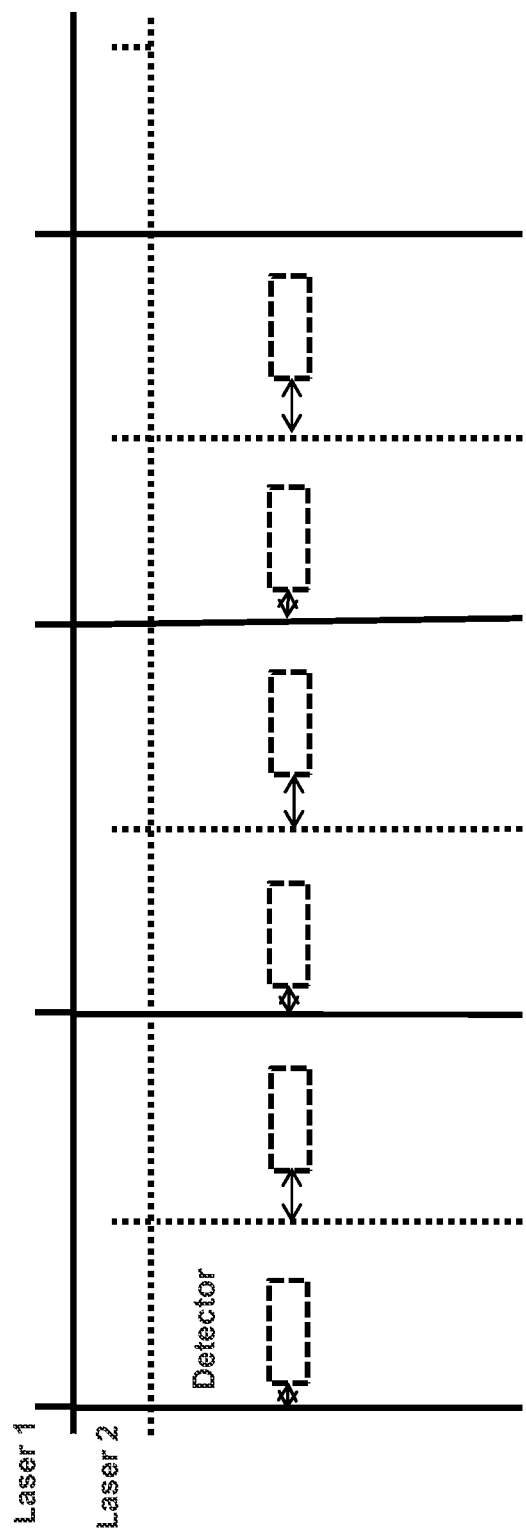
FIG. 8c schematically depicts the relationship of detection windows of one detector to different lasers.
Figure 8D:
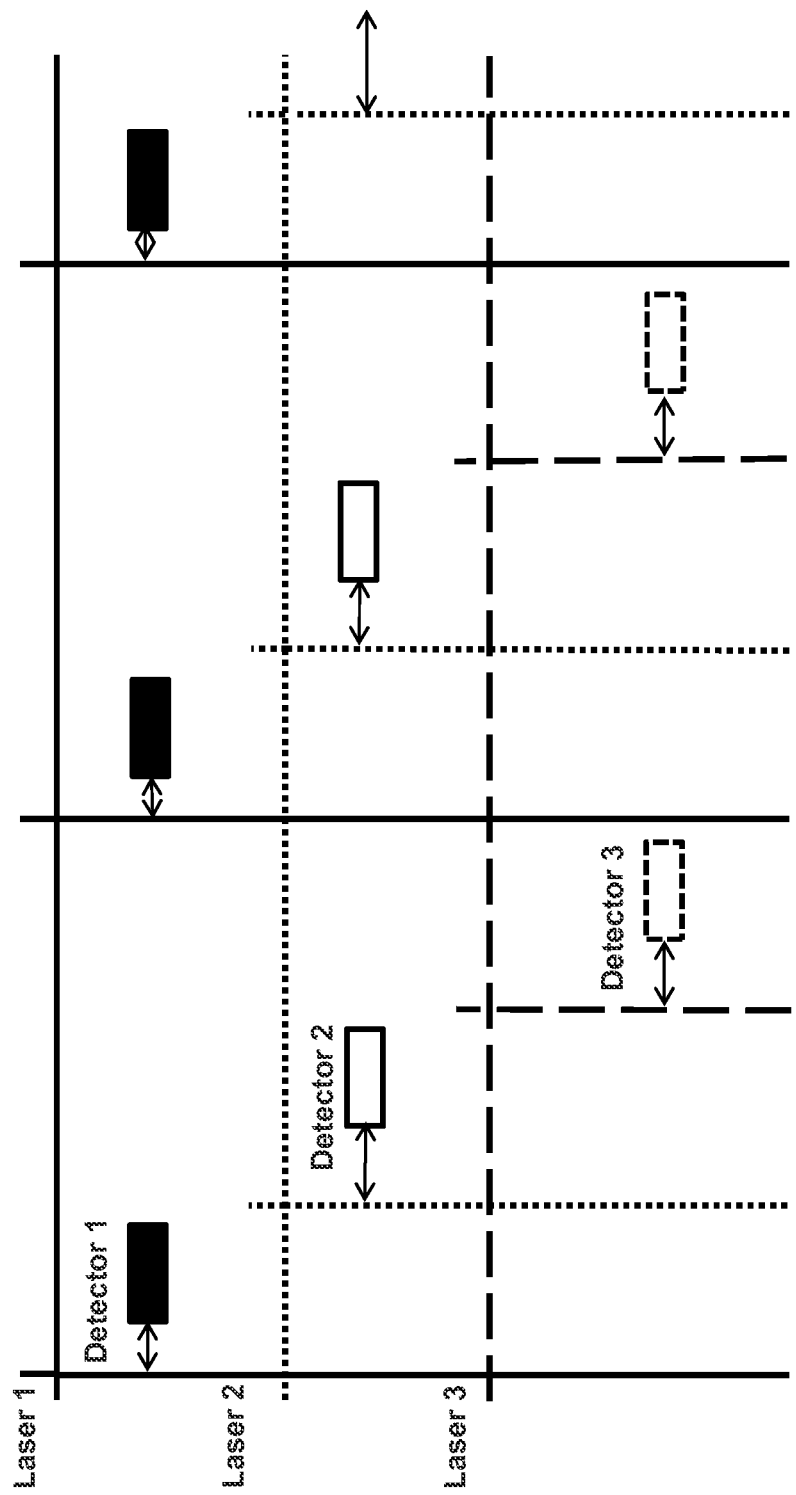
FIG. 8d schematically depicts the removal of cross-signals by sequential image acquisition on one signal.
Figure 8E:
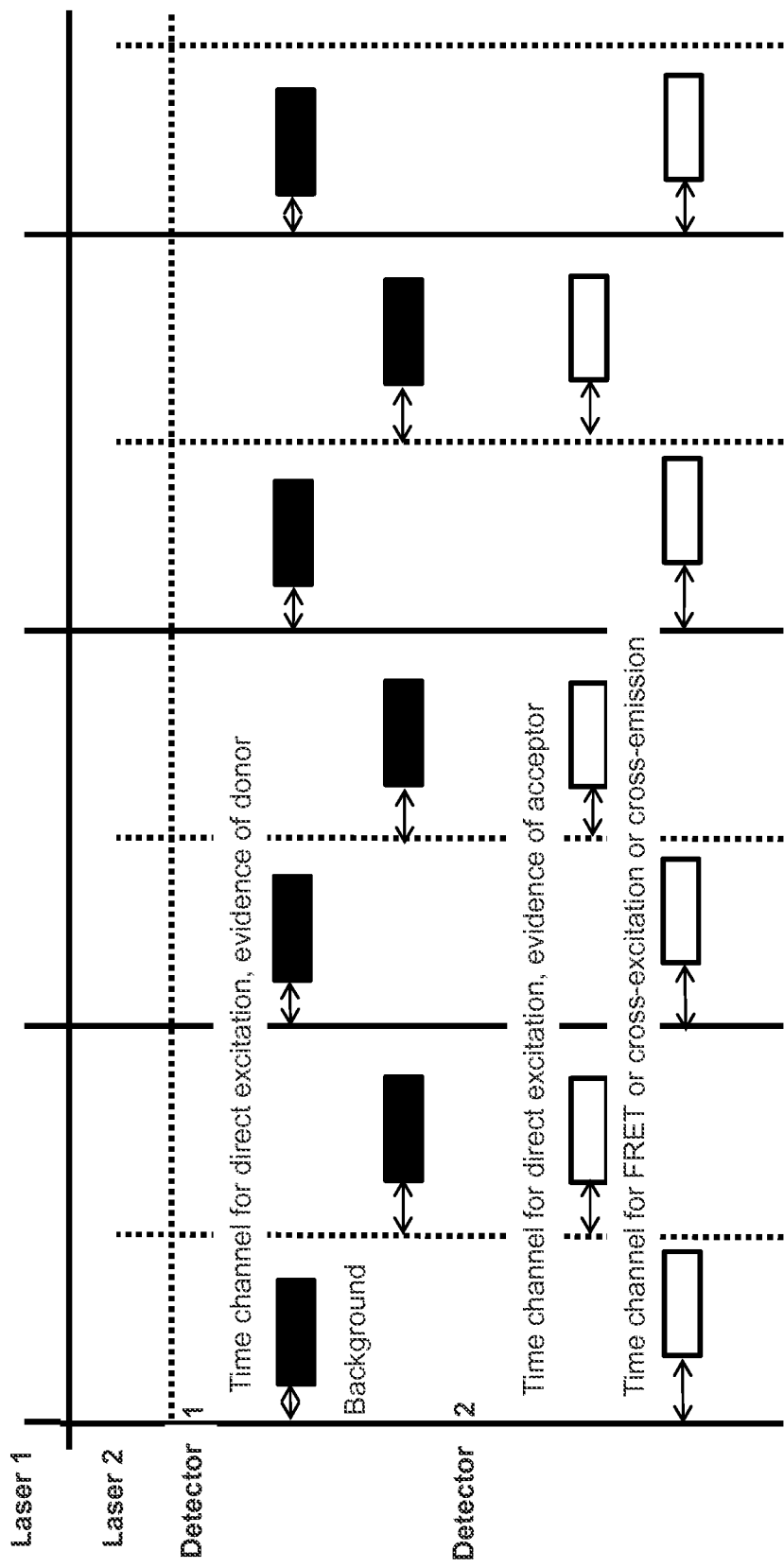
FIG. 8e schematically depicts the use of cross-signals for data evaluation in a context of sequential image acquisition on one pixel.

If multiple pulsed lasers are present in the system, these can pulse (i.e. emit excitation light) simultaneously or alternatingly in a sequence selectable by the user. The temporal detection windows, settable by the user, of the various detectors can all relate to one laser (see FIG. 8*a*). It is also possible for the temporal detection windows of different detectors to relate to different lasers (see FIG. 8*b*), or for the temporal detection windows of one or more detectors to relate alternatingly to different lasers (see FIG. 8*c*). This flexible association of the temporal relationship of laser pulse and temporal detection window makes possible, inter alia, a sequential data acquisition at the pixel level (see FIG. 8d). As a result, cross-excitation and cross-emission from fluorochromes located spectrally close together can be separated from one another at a hardware level. As compared with line-by-line or image-by-image sequential scanning, no pixel offset between the individual detection channels occurs for fast-moving samples with pixel-by-pixel sequential data acquisition. If the cross-excitation and cross-emission channels are also acquired, online data acquisition allows a distinction between "normal" cross-emission and FRET emission (see FIG. 8e). In all of FIGS. 8a to 8e, the time axis proceeds from left to right and the horizontal or X axis constitutes the time axis.

The depiction of anisotropy phenomena constitutes a further application. Anisotropies can result in longer or shorter decay times for dyes. The method presented does not serve to quantify the lifetime, but changes in lifetime can effectively be made visible by simply dividing the short-lived intensity by the long-lived intensity.

Gated FCS constitutes a further application. With very weak FCS samples, scattered light due to water can influence the measurement results. This scattered light can easily be identified by temporal selection during the FCS measurements, and can be made invisible to the detection channel. The influence of interfering autofluorescence can additionally be minimized by suitable selection of the FCS detection time window.

Detection separation after temporal arrival of the photons is accomplished in the electronic system downstream from the detector. Both a parallel and a sequential configuration of the electronic system are conceivable in principle.

With a sequential configuration, the pulses emitted from the light source and arriving from the detector unit are sampled by fast sampling units working in serial/parallel fashion. The pulses can be scanned by very fast ADC modules, and the arrival times of the pulses can be ascertained via corresponding processing algorithms. The time span or time spans between the pulse from the light source and the pulse or pulses from the detection unit are then ascertained. This information regarding time spans can be associated, using suitable methods, with the corresponding time segments or detection windows.

Figure 3:
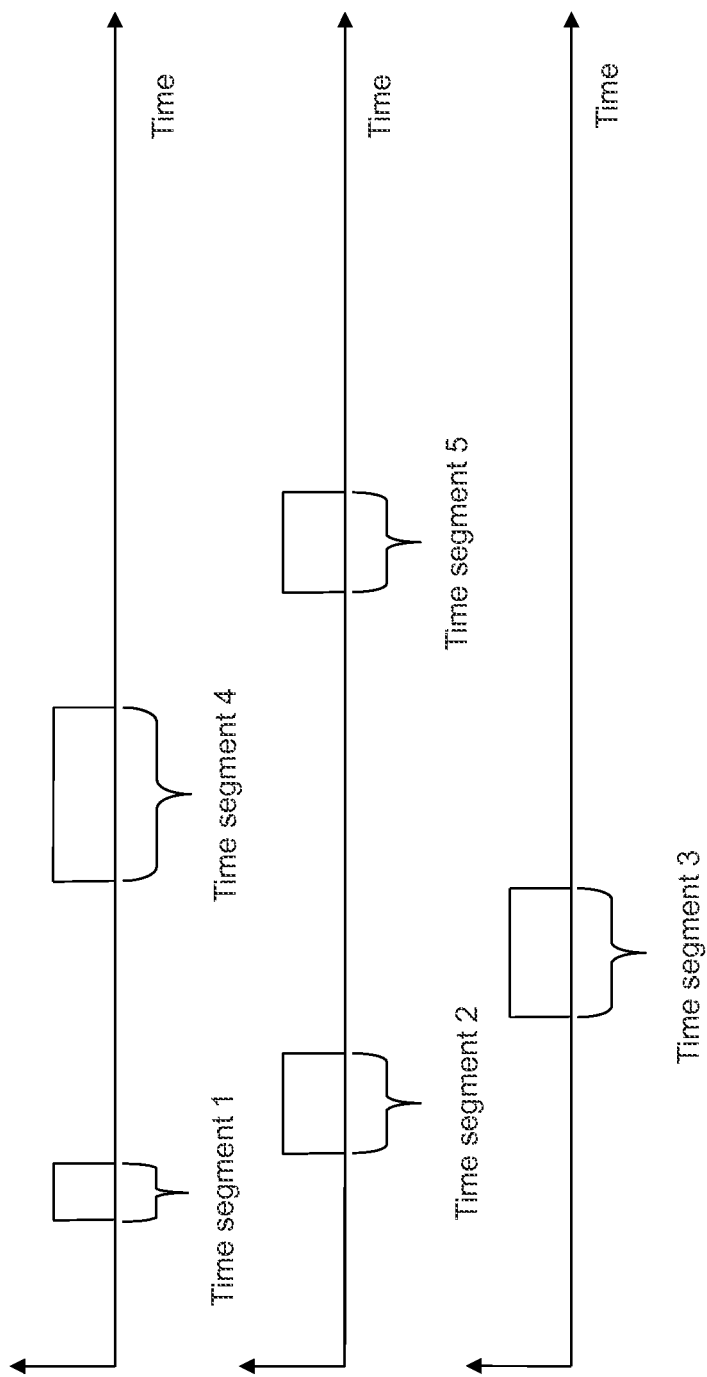
FIG. 3 is a diagram showing an exemplifying embodiment of an arrangement of three evaluation channels for a parallel evaluation.

A parallel configuration could be implemented in accordance with FIG. 3. The time segments of the sample emissions can be represented here by electrical signals. One or more time windows or detection windows is or are associated with each electrical evaluation channel. These evaluation channels can be used to control further electrical circuit elements that carry out the evaluation of the image information. FIG. 3 shows three evaluation channels having a total of five time segments or detection windows distributed among the three evaluation channels. The number of evaluation channels and time segments is not limited to the number depicted, however, but is selected merely by way of example.

Figure 4:
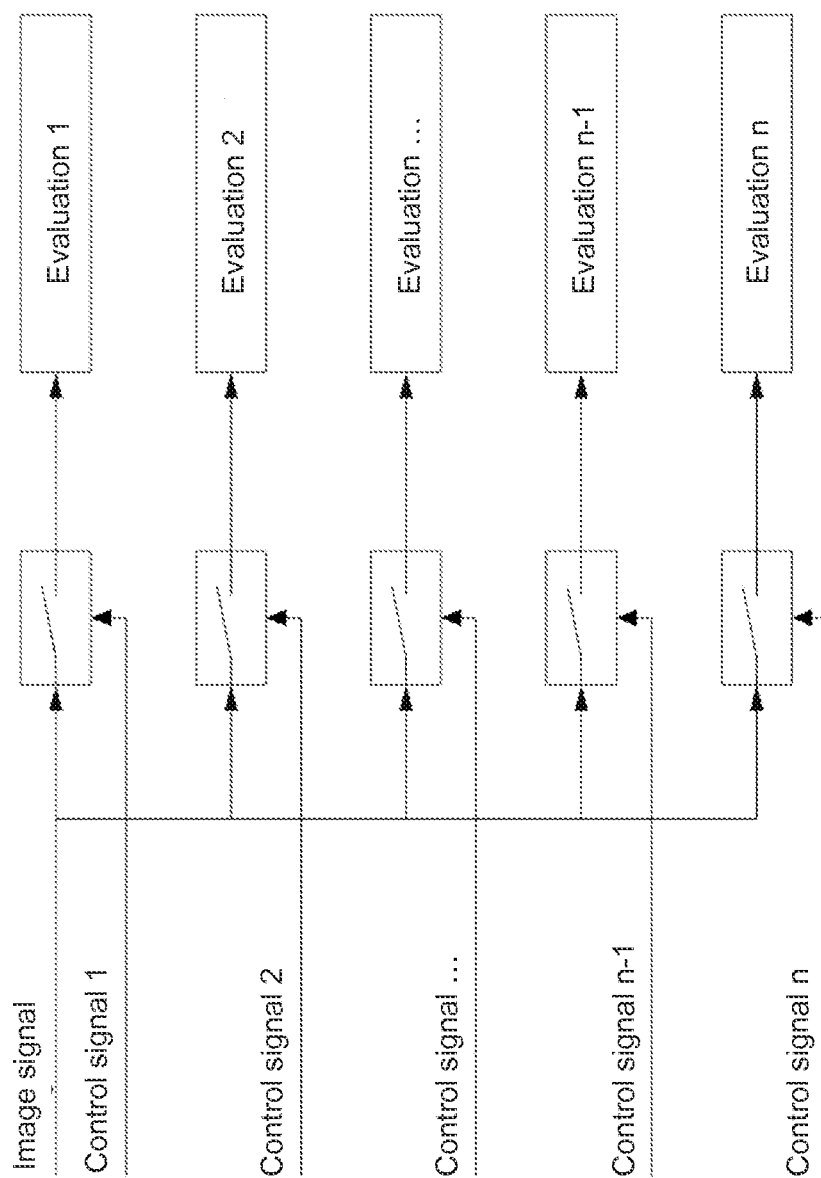
FIG. 4 schematically depicts a parallel evaluation.

Each of the evaluation channels that is illustrated controls a separate electronic evaluation system. Each time segment starts and stops evaluation of the detected signal, or confocal signal in the case of confocal microscopy. FIG. 4 shows in this regard an example of a parallel evaluation that is activated by the respective control signals. With the arrangement depicted, a previously specified spectral channel can be broken down into any number of time segments, and those time segments can be evaluated separately from one another. The arrangement shown, comprising a control logic and evaluation system, is implemented for each spectral detection channel.

An inverted application can also alternatively be effected, so that evaluation can be stopped with the aid of the control signals and thus specific signal components can be deliberately blanked out.

Figure 5:
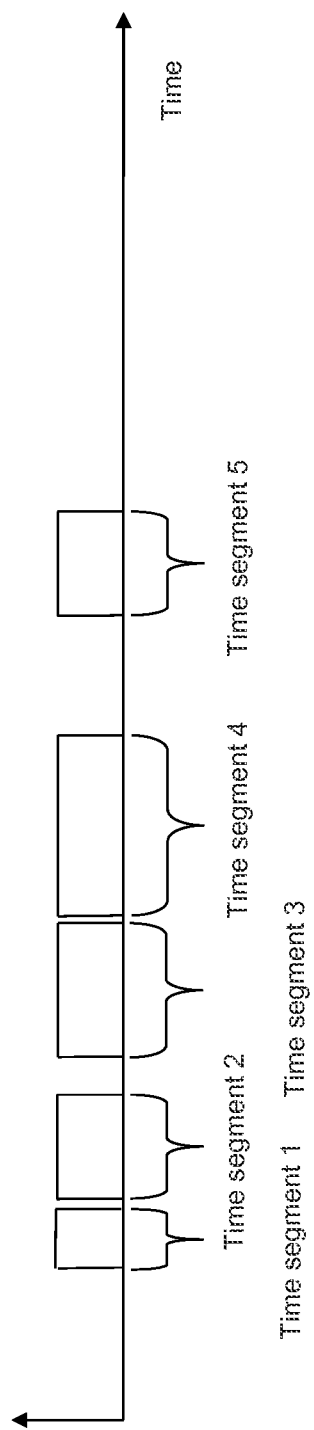
FIG. 5 is a diagram showing the time sequence of detection windows in the context of a serial evaluation.

With serial evaluation, the evaluation can be accomplished in accordance with FIG. 5. Here only one control signal exists for one evaluation channel. All the time segments to be detected are established within this control signal.

Figure 6:
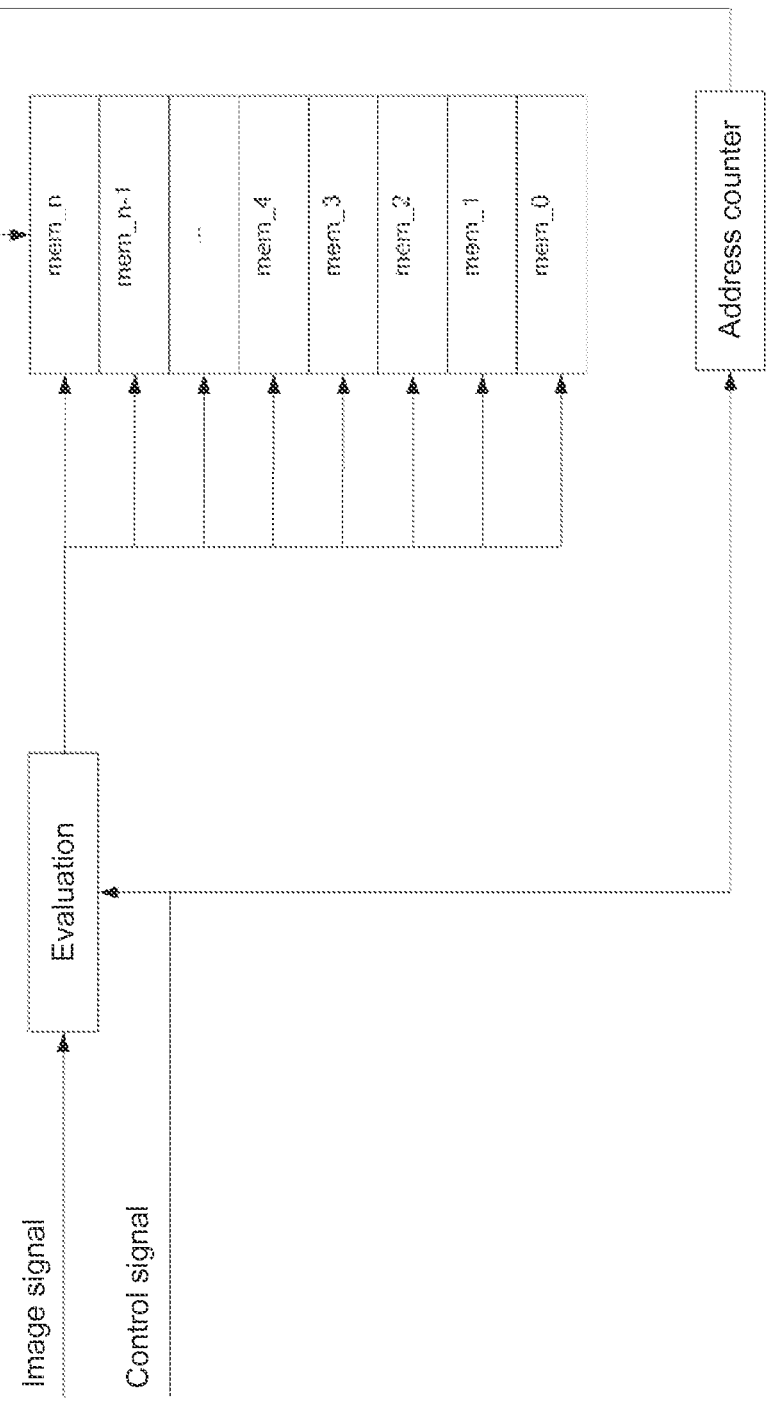
FIG. 6 schematically depicts a serial evaluation.

A control signal of this kind is used to control an electronic evaluation system. In order to achieve separate depiction of the individual time segments during image acquisition, an address counter is incremented with each deactivation of the control signal at the end of a time segment. The general configuration of the arrangement is shown in FIG. 6, in which the serial evaluation and the incrementing of the address counter are particularly evident.

As a result of the incrementing of the address counter, the image information evaluated for each time segment is located in a separate memory cell. If multiple time segments are to be grouped together, as is possible with parallel evaluation, this can be achieved by subsequent correlation of the contents of the pertinent memory cells.

With serial evaluation it is likewise possible to implement an inversion of the evaluation, allowing targeted suppression of specific time segments of the image signal. For this, a memory cell is equipped with a mark that makes it possible, in the subsequent evaluation, to subtract the content of that time segment from the overall image.

Figure 7:
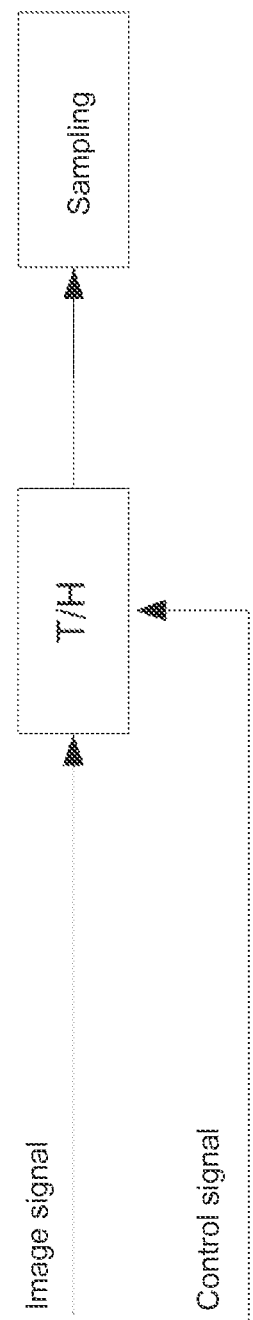
FIG. 7 schematically depicts a track-and-hold circuit.

Another type of evaluation can be implemented, as shown in FIG. 7, with a track-and-hold circuit. Here a gating signal is delivered as a serial signal to the clock input of a track-and-hold stage T/H.

Each time a gating pulse starts, accumulation of image data in the track-and-hold stage is started. At the end of the time window, the charge contained in the memory of the track-and-hold stage is sampled by an analog/digital converter and further processed. The result of this type of signal processing is a value, integrated over the gating interval, that is proportional to the detected number of photons.

To avoid repetition, reference is made to the general portion of the description, and to the appended claims, regarding further advantageous embodiments of the teaching of the present invention.

Lastly, it is expressly noted that the exemplifying embodiments described above serve only for discussion of the teaching claimed, but do not limit the latter to the exemplifying embodiments.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

PARTS LIST

1 Wavelength region
2 Wavelength region
Ch.1 Detection channel
Ch.2 Detection channel
Ch.1.1 Detection channel
Ch.1.2 Detection channel
Ch.1.3 Detection channel
Ch.2.1 Detection channel
Ch.2.2 Detection channel
Ch.2.3 Detection channel

The invention claimed is:

1. A microscope comprising:
a laser configured to generate an illumination light for a sample; and
a detection device configured to detect a signal from the sample,
wherein the detection device includes two or more adjustable spectral detection channels configured to detect predefinable different wavelength regions, and
wherein two or more temporal detection windows are respectively settable for the spectral detection channels,
wherein the wavelength regions of the spectral detection channels, the temporal detection windows, or the wavelength regions of the spectral detection channels and the temporal detection windows are, during a measurement, at least one of adjustable, depictable, or adjustable and depictable.

2. The microscope of claim 1, wherein
the wavelength regions,
the temporal detection windows, or
the wavelength regions and the temporal detection windows,
each have a different size.

3. The microscope of claim 1, wherein a separate electronic evaluation system or a separate evaluation channel is associated, or multiple separate evaluation channels are associated, with each spectral detection channel.

4. The microscope of claim 3, wherein the evaluation in the electronic evaluation system, or in the one or more evaluation channels, is activatable or deactivatable using one or more control signals temporally correlating with the temporal detection windows.

5. The microscope of claim. 1, wherein two or more temporal detection windows are mutually correlatable during or after a data acquisition.

6. The microscope of claim 1, wherein different lasers are associatable with different temporal detection windows.

7. A method for investigating a sample with a microscope, the microscope including a laser configured to generate an illumination light for a sample and including a detection device for detected signals from the sample, wherein the detection device includes two or more adjustable spectral detection channels for detecting predefinable different wavelength regions, the method comprising:
respectively setting more than one temporal detection windows for the spectral detection channels;
acquiring detected signals in the temporal detection windows; and
during a measurement, adjusting, depicting or adjusting and depicting at least one of the wavelength regions of the spectral detection channels, the temporal detection windows, or the wavelength regions of the spectral detection channels and the temporal detection windows.

8. The method of claim 7, further comprising:
evaluating the detected signals serially or in parallel.

9. The method of claim 7, wherein a separate electronic evaluation system or a separate evaluation channel is associated, or multiple separate evaluation channels are associated, with each spectral detection channel of the microscope.

10. The method of claim 9, wherein an evaluating in the electronic evaluation system, in the evaluation channel, or in the evaluation channels is activated or deactivated using one or more control signals temporally correlating with the temporal detection windows.

11. The method of claim 8, wherein the evaluating is serial, and the method further comprises:
incrementing an address counter upon each deactivation of the control signal at an end of a temporal detection window.

12. The method of claim 7, wherein each memory cell including an evaluated image information item of a temporal detection window is equipped with an individually predefinable mark.

13. The method of claim 7, further comprising:
evaluating the detected signals using a track-and-hold circuit, a data accumulation being started with each start of a gating pulse.

14. The method of claim 7, further comprising:
mutually coordinating two or more temporal detection windows during or after data acquisition.

15. The method of claim 7, wherein different lasers are associated with different temporal detection windows.

16. The microscope of claim 1, which is a confocal microscope.

17. The microscope of claim 3, wherein one temporal detection window is associated with each evaluation channel.

18. The microscope of claim 3, wherein more than one temporal detection window is associated with each evaluation channel.

19. The microscope of claim 1, wherein two or more temporal detection windows are mutually correlatable during or after a data acquisition, and correlation results are depictable.

* * * * *